(12) United States Patent
Ha et al.

(10) Patent No.: US 11,980,733 B2
(45) Date of Patent: May 14, 2024

(54) APPARATUS FOR FORMING DELIVERY PATH FOR COMPOSITION FOR TREATMENT AND AUXILIARY ASSEMBLY FOR SKIN TREATMENT INCLUDING SAME

(71) Applicant: LUTRONIC CORPORATION, Goyang (KR)

(72) Inventors: Tae Ho Ha, Goyang (KR); Bon Cheol Goo, Seoul (KR)

(73) Assignee: Lutronic Corporation, Goyang (KR)

( * ) Notice: Subject to any disclaimer, the term of this patent is extended or adjusted under 35 U.S.C. 154(b) by 605 days.

(21) Appl. No.: 16/737,720

(22) Filed: Jan. 8, 2020

(65) Prior Publication Data

US 2020/0139096 A1 May 7, 2020

Related U.S. Application Data

(62) Division of application No. 15/505,058, filed as application No. PCT/KR2015/008667 on Aug. 19, 2015, now abandoned.

(30) Foreign Application Priority Data

Aug. 19, 2014 (KR) .................. 10-2014-0108006

(51) Int. Cl.
*A61M 37/00* (2006.01)
*A61B 18/00* (2006.01)
(Continued)

(52) U.S. Cl.
CPC ........... *A61M 37/00* (2013.01); *A61B 18/203* (2013.01); *A61K 8/0225* (2013.01);
(Continued)

(58) Field of Classification Search
None
See application file for complete search history.

(56) References Cited

U.S. PATENT DOCUMENTS

| 2003/0099675 | A1 | 5/2003 | Jeong et al. |
| 2007/0134336 | A1* | 6/2007 | Worle .................. B01J 13/02 424/489 |

(Continued)

FOREIGN PATENT DOCUMENTS

| KR | 20010100194 | 11/2001 |
| KR | 100779954 | 11/2007 |

(Continued)

OTHER PUBLICATIONS

Hielscher. "Ultrasonic Treatment of Nanoparticles for Pharmaceuticals" <https://www.hielscher.com/ultrasonic-treatment-of-nanoparticles-for-pharmaceuticals.htm> available Mar. 11, 2014; accessed Jun. 29, 2023 (Year: 2014).*

(Continued)

*Primary Examiner* — Nicole P Babson

(57) ABSTRACT

The present invention relates to an apparatus for forming a delivery path for a composition for treatment and an auxiliary assembly for skin treatment including the same, and provides an apparatus for forming a delivery path for a composition for treatment and an auxiliary assembly for skin treatment including the same, the apparatus comprising: a light source; a light irradiating unit for receiving a light from the light source to irradiate the light on a surface of skin; and a control unit for controlling a pulse waveform of a light irradiated through the light irradiating unit so as to form a plurality of pores, which form a path through which a composition applied on the surface of the skin is transferred inside, on the surface of the skin after irradiating the light.

12 Claims, 6 Drawing Sheets

(51) Int. Cl.
  *A61B 18/20* (2006.01)
  *A61K 8/02* (2006.01)
  *A61K 8/37* (2006.01)
  *A61K 8/41* (2006.01)
  *A61K 8/42* (2006.01)
  *A61K 8/44* (2006.01)
  *A61K 8/67* (2006.01)
  *A61K 8/68* (2006.01)
  *A61K 8/73* (2006.01)
  *A61K 31/07* (2006.01)
  *A61K 31/195* (2006.01)
  *A61K 31/375* (2006.01)
  *A61K 31/728* (2006.01)
  *A61Q 19/00* (2006.01)

(52) U.S. Cl.
  CPC .......... *A61K 8/0245* (2013.01); *A61K 8/0295* (2013.01); *A61K 8/375* (2013.01); *A61K 8/41* (2013.01); *A61K 8/42* (2013.01); *A61K 8/44* (2013.01); *A61K 8/671* (2013.01); *A61K 8/676* (2013.01); *A61K 8/68* (2013.01); *A61K 8/735* (2013.01); *A61K 31/07* (2013.01); *A61K 31/195* (2013.01); *A61K 31/375* (2013.01); *A61K 31/728* (2013.01); *A61Q 19/00* (2013.01); *A61B 2018/0047* (2013.01); *A61K 2800/81* (2013.01); *A61M 2037/0007* (2013.01); *A61M 2202/064* (2013.01)

(56) References Cited

U.S. PATENT DOCUMENTS

| | | | |
|---|---|---|---|
| 2008/0058783 A1* | 3/2008 | Altshuler | A61B 18/20 606/9 |
| 2008/0300582 A1 | 12/2008 | Park | |
| 2009/0053290 A1* | 2/2009 | Sand | A61K 8/34 514/159 |
| 2012/0121725 A1* | 5/2012 | Garnier | A61K 8/645 424/642 |

FOREIGN PATENT DOCUMENTS

| | | |
|---|---|---|
| KR | 20110015986 A | 2/2011 |
| KR | 20120139137 | 12/2012 |
| KR | 20140027790 A | 3/2014 |
| WO | WO2012173458 A2 | 12/2012 |

OTHER PUBLICATIONS

International Search Report for International Patent Application No. PCT/KR2015/008667 filed Aug. 19, 2015.

* cited by examiner

APPARATUS FOR FORMING DELIVERY PATH FOR COMPOSITION FOR TREATMENT AND AUXILIARY ASSEMBLY FOR SKIN TREATMENT INCLUDING SAME

CROSS-REFERENCE TO RELATED APPLICATION

This application is a divisional application of Ser. No. 15/505,058, which is a national stage application, filed under 35 U.S.C. § 371, of International Patent Application No. PCT/KR2015/008667 filed on Aug. 19, 2015, which claims the priority of Korean application No. 10-2014-0108006 filed on Aug. 19, 2014, the contents of which are incorporated by reference.

BACKGROUND OF THE INVENTION

Field of the Invention

The present invention relates to an apparatus for forming a delivery path for a composition for treatment and an auxiliary assembly for skin treatment including the same, and more specifically, to an apparatus for forming a delivery path for a composition for treatment for improving skin absorption of a composition for treatment and an auxiliary assembly for skin treatment including the same.

Related Art

Recently, with a growing interest in skin, the interest in compositions for skin treatment for protecting skin and improving skin conditions is also significantly increasing. These compositions for skin treatment employ various components and thus various functional products specialized for skin characteristics, skin lesions, or purposes of improvement are being developed. Recently, cosmeceutical products including professional therapeutic functions beyond the realm of simple functional cosmetics are being developed.

Generally, compositions for skin treatment are used in such a manner they are applied on a skin surface of a patient. Then, part of the applied compositions for skin treatment is absorbed into skin tissue and involved in skin improvement.

However, in conventional cases, the percentage that a given composition applied on a skin surface arrived at a target tissue such as a dermal layer was about less than 5% and thus it was difficult to achieve a sufficient effect for the amount of use. In particular, in the case of cosmeceutical compositions where functionalities are emphasized, the percentage of components substantially involved in the functions accounts for is about 1% relative to the total composition, and the percentage that substantially contributes to skin improvement is only 0.05% or less and thus there was a problem in that the efficiency is significantly lowered.

SUMMARY OF THE INVENTION

The present invention, in order to solve the above problems, provides an apparatus for forming a delivery path for a composition for treatment, that forms a delivery path through which the composition is delivered, on a surface of skin so that the composition for skin treatment is effectively delivered to a target position thereby maximizing the therapeutic effect, and an auxiliary assembly for skin treatment including the same.

To achieve the objects, the present invention provides an apparatus for forming a delivery path for a composition for treatment, which includes a light source; a light irradiating unit for receiving a light from the light source to irradiate the light on a surface of skin; and a control unit for controlling a pulse waveform of a light irradiated through the light irradiating unit so as to form a plurality of pores, which form a path through which a composition applied on the surface of the skin is transferred inside, on the surface of the skin after irradiating the light.

In particular, the light irradiated through the light irradiating unit may be configured so that pores having a diameter of 200 μm or less can be formed on the surface of the skin. These pores may be formed so that they can be extended from the surface of the skin to a dermal tissue.

The light irradiated through the light irradiating unit may be configured to have a wavelength in a range of 1800 nm or higher to 2000 nm or less. In particular, the light source of the light irradiating unit may be configured to include laser diode.

Additionally, the composition described above may be prepared by mixing a powder-type preparation with a solvent followed by stirring. The powder-type preparation may be formed to have a cubosome-type structure.

In particular, the composition described above may consist of only one selected from vitamin C, retinol, tranexamic acid, ceramide, and hyaluronic acid.

Meanwhile, the object of the present invention described above may also be achieved by a composition for skin treatment, which consists of a powder-type preparation and a solvent for dissolving the powder-type preparation, applied to the skin where pores were formed by laser, and is transferred inside of the skin.

Furthermore, the object of the present invention described above may also be achieved by an auxiliary assembly for skin treatment, which includes: a stirrer for preparing a composition for treatment by stirring a powder-type preparation and a solvent; and an apparatus for forming a delivery path for a composition for treatment, which includes a light source; a light irradiating unit for receiving a light from the light source to irradiate the light on a surface of skin; and a control unit for controlling a pulse waveform of a light irradiated through the light irradiating unit so as to form a plurality of pores, which form a path through which the composition for treatment is applied and transferred inside, on the surface of the skin.

Lastly, the object of the present invention described above may also be achieved by a method for skin treatment, wherein the method includes: a step of forming a plurality of pores on a surface of skin using an apparatus for forming a delivery path for a composition for treatment; a step of preparing a composition for treatment by stirring a powder-type preparation along with a solvent; and a step of applying the composition for treatment on the surface of the skin so that the composition for treatment can be injected into the plurality of pores.

According to the present invention, a delivery path for a composition for treatment is formed by an apparatus for forming a delivery path for a composition for treatment and an auxiliary assembly for skin treatment, and thus the composition can be easily transferred up to a target tissue along the path. Therefore, the present invention has an advantage in that the effects of treating and improving skin can be maximized even by using a small amount.

DESCRIPTION OF EXEMPLARY EMBODIMENTS

Hereinafter, an apparatus for forming a delivery path for a composition for treatment according to an embodiment of the present invention and an auxiliary assembly for skin treatment including the same will be explained in detail with reference to the accompanying drawings. In the explanation below, the positional relationship between each of constituting elements is explained in principle based on the drawings. Additionally, the drawings may be indicated by simplifying or exaggerating when necessary, the structure of the present invention for the convenience of the explanation. Accordingly, it is obvious that the scope of the present invention should not be limited thereto but the present invention may be embodied by adding, modified, or omitting various apparatuses.

Figure 1:
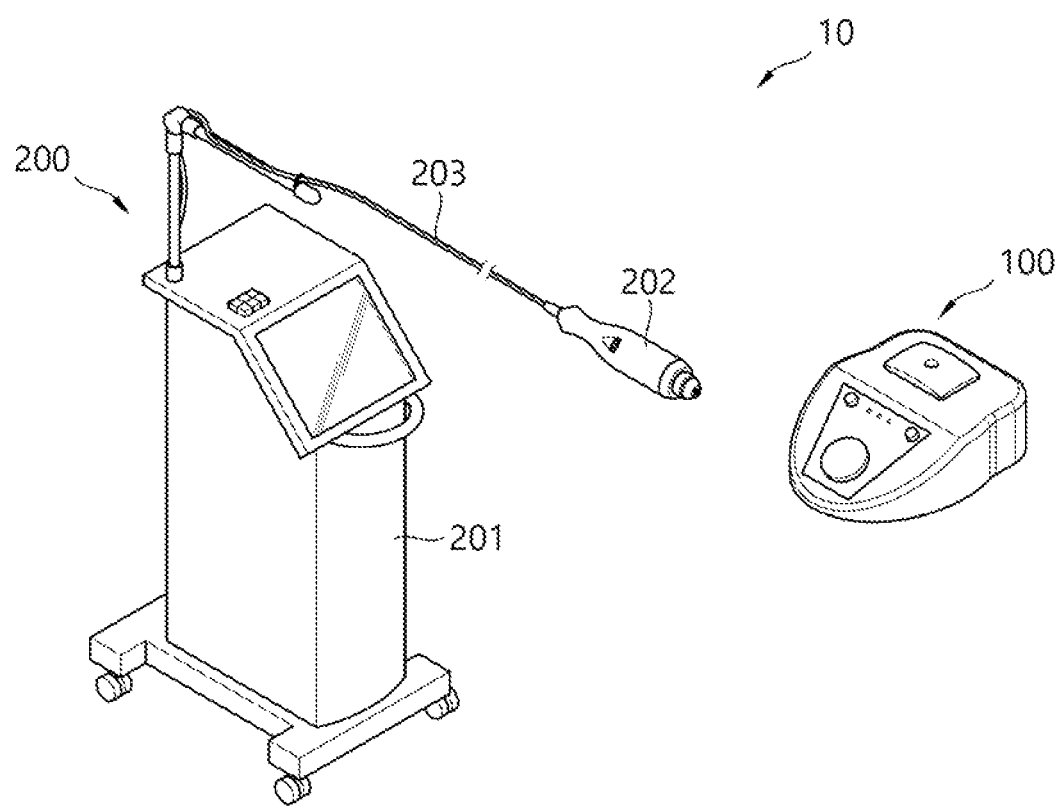
FIG. 1 is a schematic diagram illustrating an auxiliary assembly for skin treatment according to an embodiment of the present invention.

FIG. 1 shows an auxiliary assembly for skin treatment according to an embodiment of the present invention. As illustrated in FIG. 1, the auxiliary assembly for skin treatment 10 is configured to include a stirrer 100 and an apparatus for forming a delivery path for a composition for treatment 200.

In particular, the stirrer 100 is an apparatus for preparing a composition for treatment by a user. Since the auxiliary assembly for skin treatment 10 is provided to include the stirrer 100, the user can directly prepare the composition for treatment in a place for operation before the user operates the procedure.

Additionally, the apparatus for forming a delivery path for a composition for treatment 200 is an apparatus for forming a path for the composition for treatment to be delivered inside of skin, and such a path can be formed on a patient's skin using light.

Hereinafter, referring to FIGS. 2 to 4, the stirrer and the apparatus for forming a delivery path for a composition for treatment will be explained in more detail.

Figure 2:
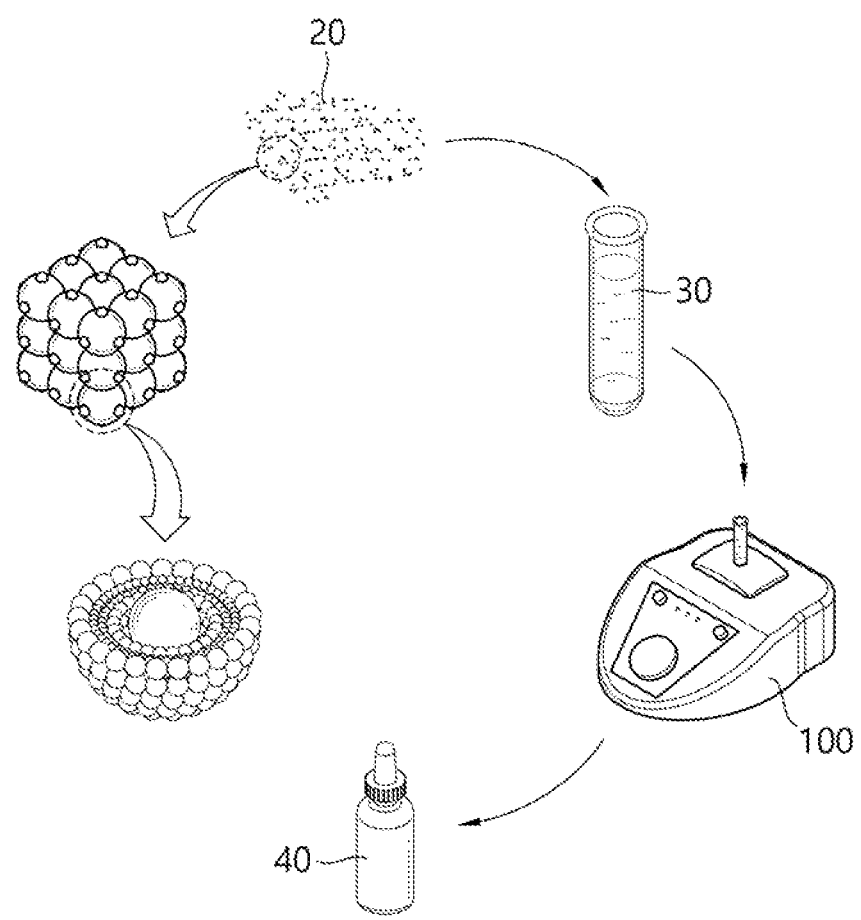
FIG. 2 is a schematic diagram illustrating the process of preparing a composition for skin treatment using a stirrer of FIG. 1.

FIG. 2 is a schematic diagram illustrating the process of preparing a composition for skin treatment using the stirrer of FIG. 1.

As illustrated in FIG. 2, the material for treatment may be provide in the form of a powder-type preparation 20. The powder-type preparation 20 is constituted to include a component material for skin treatment. For example, the powder-type preparation may be constituted to include at least one among vitamin C, retinol, tranexamic acid, ceramide, and hyaluronic acid, which have skin treatment effects.

For example, in an embodiment, the powder-type preparation may be prepared in 5 different kinds, which includes a powder-type preparation including hyaluronic acid, a powder-type preparation including vitamin C, a powder-type preparation including retinol, a powder-type preparation including tranexamic acid, and a powder-type preparation including ceramide. Accordingly, a user can prepare a composition to be used for treatment by selecting any one from the 5 different kinds of powder-type preparations, in consideration of the lesions and therapeutic steps of a patient.

As described above, when a composition for treatment is prepared to proceed with a treatment being focused on a single component in an embodiment of the present invention, any one from the 5 different kinds of powder-type preparations is selected to be used, but the composition for treatment may be prepared by selecting at least two from the 5 different kinds of powder-type preparations, according to the user's selection.

The powder-type preparations 20 may be preparations which are configured to have a cubosome structure including a single active ingredient. Cubosome is a kind of nanoparticle made of glyceryl monooleate (GMO), which is a biocompatible material. Cubosome has a cubic structure in an aqueous solution due to its molecular structural specificity and has a bicontinuous aqueous channel. The drug delivery efficiency can be improved while maintaining human-friendliness by preparing the active ingredient into the nanoparticle (see FIG. 2).

The stirrer 100 is an apparatus for preparing a composition for treatment using the powder-type preparations, and it may consist of a vortex mixer. Accordingly, a user can prepare a composition for treatment 40 in a serum type by injecting the selected powder-type preparation 20 of a single ingredient and a separately-provided solvent (e.g., distilled water) into a stirrer 100 followed by stirring. The thus-prepared composition for treatment 40, being in a blended state where the powder-type preparation is dissolved in a solvent, includes particles in the form of a cubosome, and these particles may be configured to have a diameter of 200 μm or less.

The stirrer 100 may be provided as one of the constituting elements that constitutes the auxiliary assembly for skin treatment 10 but is not limited thereto and it is possible to use a self-provided stirrer.

Figure 3:
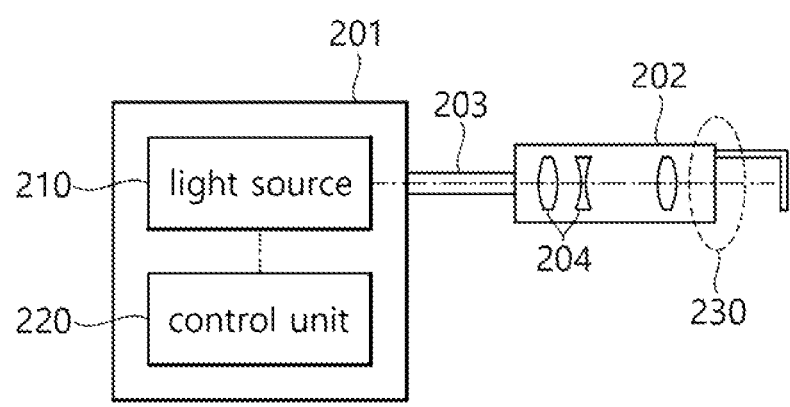
FIG. 3 is a block diagram schematically illustrating the constitution of the apparatus for forming a delivery path for a composition for treatment of FIG. 1.

FIG. 3 is a block diagram schematically illustrating the constitution of the apparatus for forming a delivery path for a composition for treatment of FIG. 1. As illustrated in FIG. 3, the apparatus for forming a delivery path for a composition for treatment 200 is configured to include a light source 210, a light irradiating unit 230, and a control unit 220.

The light source 210 generates light which is irradiated through the light irradiating unit 230. In an embodiment of the present invention, the apparatus for forming a delivery path for a composition for treatment 200 forms a delivery path on a surface of skin using laser, and accordingly, the light source 210 is configured to produce laser. More specifically, the light source 210 has excellent reactivity to water and can thus be configured to generate laser having a wavelength of 1500 nm or higher, which enables to form pores when irradiated on skin.

The light source 210 may be provided inside of the main body 201 of the apparatus for forming a delivery path for a composition for treatment 200. The light source 210 may be configured in various structures, and in an embodiment of the present invention, for example, the light source 210 may be configured by using laser diode which irradiates a laser having a wavelength of 1927 nm. However, in addition, design modification of the light source in various methods is possible, for example, the light source may be configured to be provided within the handpiece instead of the main body, and the light source may be configured to generate light having a wavelength of 1550 nm or in a range of 2700 nm to 2900 nm, etc.

The light irradiating unit 230 has a constitution that the light produced in the light source 210 is irradiated and the light irradiated through the light irradiating unit 230 is irradiated to a surface of a patient's skin. A light fiber 203 and/or a plurality of optical elements 204 are disposed between the light irradiating unit 230 and the light source 210 and they form a path for the progress of the light. According to the structure illustrated in FIG. 1, the light irradiating unit 230 is formed at the end of the handpiece 202. Accordingly, a user can proceed with the treatment in a state where the light irradiating unit 230 is disposed on the patient's skin by grapping the handpiece 202.

The light irradiated through the light irradiating unit 230 may be configured to irradiate light to a single location in a state that the handpiece 202 is being fixed, and may be configured to irradiate light on multiple locations within a region where the handpiece 202 is located.

However, since the configuration of the light source 210 is generally similar to that of an optical treatment apparatus for skin treatment, the detailed explanation is omitted herein below.

Meanwhile, the control unit 220 of the apparatus for forming a delivery path for a composition for treatment 200 controls the operation details of each constituting element including the light source 210 and the light irradiating unit 230. In particular, the control unit 220 is configured to control the operation details of the light source 210 and the light irradiating unit 230 according to the details of the input signal or predetermined mode by a user, and to control the output of the light being irradiated through the light irradiating unit 230, spot size, and the pulse waveform of light. Accordingly, the control unit can form pores, which become the delivery path of a composition for treatment, on a surface of skin by irradiating light through the control of the light source 210 and the light irradiating unit 230.

Figure 4:
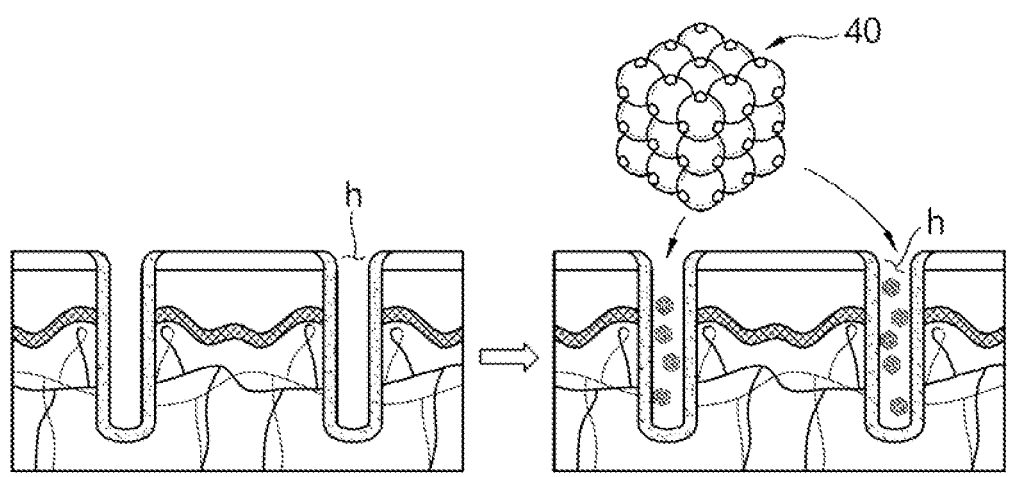
FIG. 4 is a cross-sectional diagram illustrating the feature of the delivery of a composition for skin treatment.

FIG. 4 is a cross-sectional diagram illustrating the feature of the delivery of a composition for skin treatment. As illustrated in FIG. 4 (a), the light irradiated through the light irradiating unit can be irradiated to a surface of a patient's skin thereby forming pores (h). In particular, the spot size of the light irradiated may be controlled to have a diameter of 200 μm or less, and as such, pores having a diameter in a range of 50 μm or higher to 200 μm or less may be formed on a surface of skin. When the size of the pores formed on the skin surface is within the above range, a path through which a composition for treatment can be delivered can be formed, and it is possible to have a rapid recovery without additional skin damage or scar after the procedure.

In particular, the control unit 220 can control the output or pulse waveform of light so that the pores formed on the skin surface may have a depth to be extended to a target position (e.g., a dermal tissue). In particular, it is possible to control the light irradiated through the light irradiating unit 230 to form pores with a corresponding depth by a single irradiation, and it is also possible to control to form pores with a corresponding depth by irradiating multiple shots on a single location.

When a plurality of pores extended to a target position from a patient's skin surface are formed by the method described above, the composition for treatment 40 may be delivered to a target tissue through the pores and absorbed in the target position (see FIG. 4(b)). Accordingly, there is an advantage in that the efficiency of delivering the composition for skin treatment can be significantly improved.

However, although the apparatus for forming a delivery path for a composition for treatment 200 was explained above being focused on the function of forming a delivery path of a composition for treatment on a surface of skin, it is also possible to utilize the apparatus for optical treatment of skin lesions by the control of the control unit 220. For example, in the case of a laser having a wavelength of 1927 nm in an embodiment of the present invention, due to its high water absorptivity, it is possible to treat melanin while minimizing skin damage, and thus it is possible to control to optically treat skin, in addition to the method of pore formation on a skin surface, by configuring the control unit 220 to enable the control of the light source 210 and the light irradiating unit 230.

Figure 5:
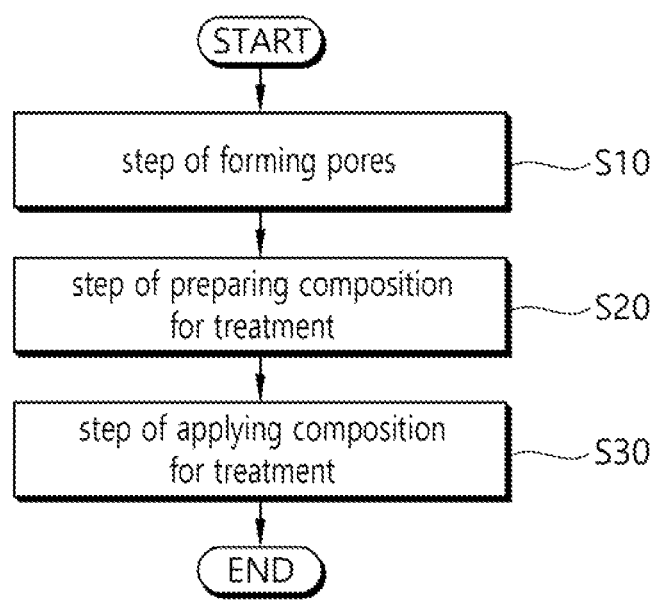
FIG. 5 is a flowchart illustrating a method for skin treatment.
Figure 6:
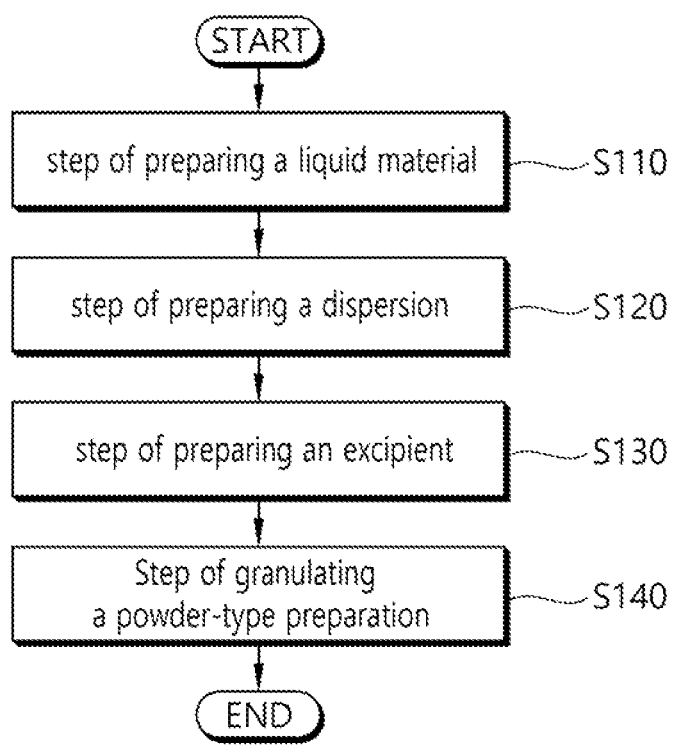
FIG. 6 is a flowchart illustrating a method for preparing a powder-type preparation.

FIG. 5 is a flowchart illustrating a method for skin treatment. Hereinafter, a method for skin treatment by applying a composition for skin treatment using the auxiliary assembly for skin treatment described above is explained in detail.

First, a step of forming a plurality of pores on a surface of a patient's skin using the apparatus for forming a delivery path for a composition for treatment 200 is performed (S10). This step is performed in such a manner that a user breaks the handpiece 202, fixes it on a skin surface of a patient who requires treatment, and irradiates light through the light irradiating unit 230. The light irradiated through the light irradiating unit is controlled to form pores having a diameter in a range of 50 μm or higher to 200 μm or less. Additionally, the pores may be formed to have a depth to be extended to a target tissue to which the composition for treatment is to be delivered. These pores may form a path (h) through which the composition for treatment is transferred inside of skin, after this step.

A step of preparing a composition for treatment may be performed (S20). In FIG. 5, this step is shown following the step of forming pores described above, however, this step is a step performed separately from the step of forming pores, and this step may possibly be performed before the step of forming pores, may possibly be performed after the step of forming pores, and may possibly be performed simultaneously by other workers.

In this step, a composition for treatment 40 is prepared using the powder-type preparations 20 provided in a pre-prepared form. These powder-type preparations are configured to have a cubosome structure and they may be those which include one from vitamin C, retinol, tranexamic acid, ceramide, and hyaluronic acid, as an active ingredient. A user may prepare a composition for treatment by selecting one from the 5 kinds of powder-type preparations having different active ingredients as described above, in consideration of the skin conditions and treatment steps of a patient.

In this step, a user injects the selected powder-type preparation 20 along with distilled water, which corresponds to a solvent, to a stirrer 100. Then, the selected powder-type preparation 20 and the solvent are dissolved by stirring for 3 to 5 minutes using a stirrer. As such, a composition for treatment 40 in a serum type is prepared. The thus-prepared composition for treatment includes particles having a cubosome structure. These particles may be configured to have a diameter of 200 μm or less. As such, the composition for treatment is not distributed in a pre-prepared from but is directly prepared via on-site production by a user immediately before skin treatment. Accordingly, there is an advantage in that the treatment can be proceeded in a state where the effect of the composition for treatment is in an optimal state.

Meanwhile, when a composition for treatment is completed by going through with the steps described above and pores are formed on a skin surface of a patient, the user proceeds with a step of applying the prepared composition for treatment on the skin surface of a patient (S30). The composition for treatment applied on the skin surface of a patient can be delivered to a target tissue through the delivery path formed by the pores (h) on the skin surface and absorbed by the target tissue.

As described above, the present invention provides an auxiliary assembly for skin treatment capable of improving the therapeutic effect using a composition for treatment in proceeding with skin treatment, and a method for treatment using the same.

As such, the path through which the composition for treatment is directly delivered to the target tissue is formed through the pretreatment process. In this case, a significantly higher amount of the composition for treatment can be delivered to the targeted position even when a small amount of the composition is used, compared to when the composition for treatment penetrates the skin and then arrives at the target tissue thus being capable of improving the therapeutic effect. Additionally, due to the use of the composition for treatment after the direct on-site production, it is possible to proceed with the optimal treatment using a fresh composition not containing any preservatives, etc.

Hereinafter, a method for preparing a powder-type preparation for skin treatment, which is used for preparing the composition for the treatment described above, is explained in detail.

However, it should be noted that the powder-type preparation explained herein below is one which is independently prepared by a supplier and distributed to users, unlike the composition described above which is directly prepared by a user before performing the treatment.

As described above, these powder-type preparations are constituted to include any one among hyaluronic acid, vitamin C, retinol, tranexamic acid, and ceramide as an active ingredient. Herein below, each of the preparation methods for the powder-type preparations containing hyaluronic acid as an active ingredient is explained.

Methods of Preparing Powder-Type Preparations Containing Hyaluronic Acid

First, a step of preparing a liquid material, which includes an ingredient material contained in the powder-type preparation, is included (S110). The liquid material may be constituted to include an ingredient material for skin treatment, which includes glycerin in a monoolein-melt solution, so as to form a cubosome structure being made of glyceryl monooleate (GMO). The step may consist of a step of preparing an oil phase solution and a step of preparing a water phase solution.

In particular, with respect to the step of preparing an oil phase solution, d-panthenol and squalane are added to monoolein, which is in a state melted in a water bath at room temperature or higher, and the mixture is stirred using a stirrer and thereby an oil phase solution can be prepared.

In particular, monoolein is a material which forms a cubic phase when it establishes an equilibration with an adequate or higher amount of water and it can form a structural backbone. The cubic phase formed by monoolein is optically transparent and has water channels that traverse between them. The cubic phase has a water channel in a lipid matrix and thus it can load a water-soluble compound in the water channel while loading a lipid-soluble compound in the lipid matrix and thus can be used as a drug carrier.

Additionally, d-panthenol is a material which has the effects of promoting cell growth, moisturization, and wound healing, and squalane is a natural fat component which can supply oil fractions that smoothen skin.

Meanwhile, the step of preparing a water phase solution may be proceeded by heating a mixture of distilled water, glycerin, and a surfactant, which are contained in a separate container apart from that for the oil phase solution, at room temperature or higher. In particular, poloxamer P407 may be used as the surfactant.

Once a liquid material is prepared through the process described above, a step of preparing a dispersion may be performed using the material (S120). In this step, an oil phase solution is added to the water phase solution prepared in the above step and blend them using a stirrer to produce a mixed solution. In the mixed solution, a process that the oil phase particles of the oil phase solution are fractionated by a surfactant is performed.

In this embodiment, a dispersion including nano-sized liquid crystal particles can be prepared by fractionating the oil phase particles to a nano size by additionally providing sonication to such a mixed solution. For example, in an embodiment, a dispersion including nano-sized particles was prepared by providing sonication having a frequency in a range of 10 to 100 KHz for 30 minutes.

Then, a step of preparing an excipient is performed apart from the dispersion (S130). In particular, the excipient may be constituted to include non-essential amino acids, and in this embodiment, the preparation of the excipient may be performed in such a manner that glycine, proline, $Na_2HPO_4 \cdot 7H_2O$, $KH_2PO_4$, and hyaluronic acid are mixed in a predetermined amount. However, the ingredients that constitute the excipient may be constituted by adding other ingredient(s) in consideration of therapeutic effects.

Once the dispersion and excipient are prepared by the steps described above, a step of granulating a powder-type preparation can be performed using the same (S140). The step of granulating of a powder-type preparation may be performed using a fluidized-bed granulator. The granulation process may be performed in a state where the excipient is injected into the fluidized-bed granulator by spraying the prepared dispersion. In particular, the granulation serves the role of a binder and thereby the granulation of the dispersion and excipient can be proceeded, and drying is proceeded simultaneously during the granulation process and thereby a powder-type preparation is prepared.

The powder-type preparation containing hyaluronic acid prepared by the above process can deliver hyaluronic acid to skin tissue and provide an environment where moisture can be retained in the dermis thereby being capable of maintaining moist and healthy skin, and in particular, being capable of sustaining the skin structure thereby exhibiting an effect of preventing skin wrinkles.

Method of Preparing a Powder-Type Preparation Containing Tranexamic Acid

The method of preparing a powder-type preparation containing tranexamic acid is proceeded in a manner similar to that of preparing a powder-type preparation containing hyaluronic acid described above.

However, in the step of preparing a water phase solution during the step of preparing a liquid phase material, the step is proceeded in such a manner that a mixture, which is in a state further mixed with tranexamic acid, in addition to distilled water, glycerin, and a surfactant, is heated to a room temperature or higher.

Additionally, in the step of preparing an excipient, the preparation is proceeded in such a manner that not only glycine, proline, $Na_2HPO_4 \cdot 7H_2O$, $KH_2PO_4$, and hyaluronic acid but tranexamic acid is mixed in a predetermined amount.

Additionally, a powder-type preparation containing tranexamic acid can be prepared through the step of granulating a powder-type preparation using the dispersion and excipient prepared by the same.

The thus-prepared powder-type preparation containing tranexamic acid can deliver tranexamic acid to skin tissue and the delivered tranexamic acid acts on melanocytes within tissues to inhibit the biosynthesis of melanin thereby preventing the generation of melasma or black spot on skin and exhibiting the effect of skin whitening.

Method of Preparing a Powder-Type Preparation Containing Retinol-Vitamin A

The method of preparing a powder-type preparation containing vitamin A is proceeded in a manner similar to that of preparing a powder-type preparation containing hyaluronic acid described above.

However, in the step of preparing an oil phase solution during the step of preparing a liquid phase material, the oil phase solution can be prepared in such a manner that not only d-panthenol and squalene but also vitamin A material is added in a state where monoolein is melted by stirring using a stirrer.

Additionally, a powder-type preparation containing vitamin A can be prepared through a step of granulating the powder-type preparation using a dispersion prepared by the same.

The thus-prepared powder-type preparation containing vitamin A can deliver vitamin A to skin tissue and the delivered vitamin A can inhibit overproliferation of sebaceous gland within the tissue thereby reducing the amount of sebum secretion, normalizing the desquamation process within the tissue thereby exhibiting effects of treating acne and inhibiting wrinkle formation on skin.

Method of Preparing a Powder-Type Preparation Containing Vitamin C

The method of preparing a powder-type preparation containing vitamin C is proceeded in a manner similar to that of preparing a powder-type preparation containing hyaluronic acid described above.

However, in the step of preparing a water phase solution during the step of preparing a liquid phase material, the step is proceeded in such a manner that a mixture, which is in a state further mixed with ascorbic acid, in addition to distilled water, glycerin, and a surfactant, is heated to a room temperature or higher.

Additionally, in the step of preparing an excipient, the preparation is proceeded in such a manner that not only glycine, proline, $Na_2HPO_4 \cdot 7H_2O$, $KH_2PO_4$, and hyaluronic acid but also ascorbic acid is mixed in a predetermined amount.

Additionally, a powder-type preparation containing ascorbic acid can be prepared through the step of granulating a powder-type preparation using the dispersion and excipient prepared by the same.

The thus-prepared powder-type preparation containing vitamin C can deliver vitamin C, which is essential for cell growth and damage recovery, to skin tissue and the delivered vitamin C can inhibit the aging of skin tissue, promote collagen synthesis within the tissue, growth, differentiation, and regeneration of skin tissue, and inhibit pigmentation such as melasma, etc., thereby exhibiting the effect of skin whitening.

Method of Preparing a Powder-Type Preparation Containing Ceramide

The method of preparing a powder-type preparation containing ceramide is proceeded in a manner similar to that of preparing a powder-type preparation containing hyaluronic acid described above.

However, in the step of preparing an oil phase solution during the step of preparing a liquid phase material, the oil phase solution can be prepared in such a manner that not only d-panthenol and squalene but also ceramide is added in a state where monoolein is melted by stirring using a stirrer.

Additionally, a powder-type preparation containing ceramide can be prepared through the step of granulating a powder-type preparation using the dispersion prepared by the same.

The thus-prepared powder-type preparation containing ceramide can deliver ceramide, which constitutes the lipid component of skin, to skin tissue and the delivered ceramide can inhibit the evaporation of moisture in tissue thereby exhibiting the effects of maintaining the skin moist and preventing the occurrence of atopic dermatitis.

Although preferred embodiments of the present invention have been described above for illustrative purposes, the scope of the present invention should not be limited by the specific embodiments provided above. It would be obvious to one of ordinary skill in the art that various modifications and changes are possible, without departing from the scope and spirit of the invention as disclosed in the accompanying claims.

What is claimed is:

1. A method for skin treatment, the method comprising:
   a step of forming a plurality of pores on a surface of skin using an apparatus for forming a delivery path for a composition for treatment;
   a step of preparing the composition for treatment by stirring a powder-type preparation and a solvent for 3 to 5 minutes; and
   a step of applying the composition for treatment on the surface of the skin to inject the composition for treatment into the plurality of pores,
   wherein the composition for treatment is directly prepared by a user on-site before the user applies the composition for treatment,
   wherein the powder-type preparation is prepared by:
   preparing a liquid material comprising monoolein-melt solution by adding d-panthenol and squalene;
   preparing a dispersion using the liquid material;
   preparing an excipient comprising a therapeutic ingredient; and
   granulating the powder-type preparation using the excipient and the dispersion,
   wherein the liquid material is prepared by:
   preparing an oil phase solution comprising monoolein; and
   preparing a water phase solution comprising glycerin and a surfactant, and
   wherein the oil phase solution and the water phase solution are mixed to form a mixed solution and oil phase particles of the oil phase solution are fractionated by providing sonication to the mixed solution with a frequency from 10 to 100 kHz for about 30 minutes.

2. The method of claim 1, wherein in the step of preparing the dispersion, the oil phase particles of the oil phase solution are fractionated by the surfactant.

3. The method of claim 1, in the step of granulating the powder-type preparation, the excipient is injected into a fluidized-bed granulator by spraying the prepared dispersion, so that the powder-type preparation is granulated.

4. The method of claim 1, wherein the powder-type preparation comprises only one selected from the group consisting of vitamin C, vitamin A, tranexamic acid, ceramide, and hyaluronic acid as an effective ingredient.

5. The method of claim 4, wherein, in the step of preparing the liquid material, the liquid material comprises the effective ingredient.

6. The method of claim 4, wherein the dispersion and the excipient respectively comprise the effective ingredient.

7. The method of claim 1, wherein the powder-type preparation has a cubosome-type structure.

8. The method of claim 1, wherein in the step of forming the plurality of pores on the surface of skin, the plurality of pores have a diameter of 200 μm or less on the surface of the skin.

9. The method of claim 8, wherein the plurality of pores on the surface of the skin are formed by light having a wavelength in a range of 1800 nm or higher to 2000 nm or less irradiated from the apparatus for forming a delivery path for a composition for treatment.

10. The method of claim 1, wherein the prepared composition for treatment includes particles in the form of a cubosome and have a diameter of 200 μm or less.

11. A method for skin treatment, the method comprising:
    forming a plurality of pores on a surface of skin using an apparatus for forming a delivery path for a composition for treatment;
    preparing the composition for treatment by stirring a powder-type preparation and a solvent; and
    applying the composition for treatment on the surface of the skin to inject the composition for treatment into the plurality of pores,
    wherein the composition for treatment is directly prepared by a user on-site before the user applies the composition for treatment, and
    wherein the prepared composition for treatment includes particles in the form of a cubosome and have a diameter of 200 μm or less.

12. The method of claim 11, wherein the power-type preparation and the solvent are stirred for 3 to 5 minutes to prepare the composition for treatment.

\* \* \* \* \*